United States Patent [19]

Goure

[11] Patent Number: 4,575,565

[45] Date of Patent: Mar. 11, 1986

[54] PROCESS FOR PREPARING SUBSTITUTED BENZOTRICHLORIDES

[75] Inventor: William F. Goure, Maryland Heights, Mo.

[73] Assignee: Monsanto Company, St. Louis, Mo.

[21] Appl. No.: 723,373

[22] Filed: Apr. 15, 1985

[51] Int. Cl.$^4$ .................. C07C 41/22; C07C 17/22
[52] U.S. Cl. ............................... 568/655; 568/936; 570/183; 570/191; 570/194; 549/35
[58] Field of Search ............ 570/191, 194, 183; 568/936, 655

[56] References Cited

FOREIGN PATENT DOCUMENTS 0061029 of 0000 Fed. Rep. of Germany .

OTHER PUBLICATIONS

Seebach et al, J.A.C.S., 4303, (Dec. 1966), "Synthesis of 1-Deuterioaldehydes, Benzaldehyde-1-d.
Marhold et al, Synthesis, 951, (1982)–German Article, "Neue Methode zur Synthese von schwer zuganglichen Benzotrichloriden".
Mayer article, Chem. Ber., 98, (1965), pp. 829–837, Translated from German, "Sulfur Heterocyclics and Precursors".
Marhold, Chem. Abs., vol. 98, (1983), 16394(r).

*Primary Examiner*—Bernard Helfin
*Attorney, Agent, or Firm*—Robert B. Martin

[57] ABSTRACT

The invention herein pertains to a novel process for making substituted benzotrifluorides.

14 Claims, No Drawings

PROCESS FOR PREPARING SUBSTITUTED BENZOTRICHLORIDES

FIELD OF THE INVENTION

The present invention relates to a process for preparing substituted benzotrichloride compounds.

BACKGROUND OF THE INVENTION

Substituted benzotrichloride compounds are known in the art. These compounds are generally produced by free radical chlorination of the corresponding substituted toluene. The free radical chlorination is generally accomplished by reacting the starting compound with chlorine gas at an elevated temperature and/or in the presence of ultraviolet light or other catalyst. Free radical chlorination results generally in nonselective chlorination of alkyl substituents. Free radical chlorination also results, in some cases, in the formation of polymer by-products.

Alternative methods for making substituted benzotrichlorides are known in the art. European Patent No. 61,029 discloses chlorination of thioethers to form benzotrichlorides. Mayer et al discloses chlorination of methyl dithiobenzoates to form benzotrichlorides. Chem. Ber. 98 829 (1965).

It is an object of the present invention to provide a new process for making substituted benzotrichlorides.

Other objects and advantages will become apparent from the following disclosure.

SUMMARY OF THE INVENTION

The present invention relates to a new process for preparing substituted benzotrichloride compounds. The process generally comprises the steps of:

(a) reacting a substituted benzaldehyde with a compound having the formula HS—$(CH_2)_n$—SH in the presence of an acid; and (b) reacting the product of step (a) with a chlorinating agent to form the substituted benzotrichloride compound wherein in the above formula n is an integer from 2 to 3.

The process of the present invention can be utilized to prepare benzotrichlorides containing various types of nuclear substituents which do not react or adversely interact with the other reactants or solvents employed in the overall process.

The process of the present invention provides a unique method for making substituted benzotrichlorides.

A more thorough disclosure of the present invention is presented in the detailed description which follows.

DETAILED DESCRIPTION OF THE INVENTION

The present invention relates to a novel process for preparing substituted benzotrichloride compounds. The process generally comprises the steps of:

(a) reacting a substituted benzaldehyde with a compound having the formula HS—$(CH_2)_n$—SH in the presence of an acid; and (b) reacting the product of step (a) with a chlorinating agent to form the substituted benzotrichloride compound wherein in the above formula n is an integer from 2 to 3.

The first step of the process of the present invention generally involves reacting a substituted benzaldehyde with an alkyl dithiol in the presence of an acid to form the corresponding cyclodithioacetal. The benzaldehyde can contain a variety of nuclear substituents provided that the substituents do not adversely interact or react with the other reactants or solvents employed in the process of the present invention. Suitable nuclear substituents are lower alkyl (e.g. $C_1$–$C_4$), lower alkoxy, halo, cyano, isocyanato, and nitro. Other suitable nuclear substituents will be known to those skilled in the art.

The preferred dithiol reactant is HS—$(CH_2)_n$—SH where n is 2 or 3. Although higher alkyl dithiols can be utilized, they have greater difficulty in ring closure to form the cyclodithioacetal. Conveniently, a slight molar excess of the dithiol is utilized, e.g., 1.05 to 1.25 moles of the dithiol per mole of the substituted benzaldehyde.

The process of step (a) of the present invention is carried out in the presence of a mineral acid or Lewis acid. A suitable mineral acid is hydrochloric acid. Suitable Lewis acids are boron trifluoride or boron trifluoride etherate. Other suitable mineral acids and Lewis acids are known to those skilled in the art. A catalytic amount of the acid is utilized in the process, e.g., from 0.10 to 0.25 molar equivalents of the acid per mole of the substituted benzaldehyde.

The reaction step (a) may be conveniently carried out in the presence of a suitable organic solvent, such as hexane or other hydrocarbon solvents, benzene or alkylated benzenes, chlorinated hydrocarbons (such as chloroform or carbon tetrachloride), and other suitable solvents known to those skilled in the art.

The process step (a) is accomplished in a suitable reaction vessel equipped with means for stirring. Conveniently, the benzaldehyde and dithiol reactants are charged into the vessel with an organic solvent. A catalytic amount of an acid, such as hydrogen chloride, is then added to the reaction mixture. Preferably, anhydrous acids are utilized. Conveniently, anhydrous hydrochloric acid is bubbled through the reaction mixture for a short period of time from about 3 to about 10 minutes. The addition of the acid will normally result in a slight exotherm. After the addition of the acid, the reaction mixture is constantly stirred at room temperature for a period of time from about ½ to about 3 hours. After completion of the reaction, the product can be isolated using standard laboratory procedures. Normally, the mixture can be distilled to provide the intermediate cyclodithioacetal. The mixture, after removal of water, can also be used directly in process step (b) without intermediate cyclodithioacetal purification.

The second step of the process of the present invention involves chlorination of the cyclodithioacetal. A variety of suitable chlorinating agents can be utilized in the process of the present invention. Suitable chlorinating agents include chlorine, and sulfuryl chloride. Other suitable chlorinating agents will be known to those skilled in the art. Conveniently, a molar excess of the chlorinating agent is utilized, e.g. from 3 to about 5 molar equivalents of chlorinating agent per molar equivalent of the cyclodithioacetal reactant.

The chlorination is conveniently run in a suitable organic solvent, such as benzene, substituted benzenes for which the substituents are, for example, alkyl (e.g. $C_1$–$C_4$), halo, or nitro; hydrocarbons (e.g. $C_6$–$C_{10}$), or a chlorinated hydrocarbon, such as methylene chloride, chloroform or carbon tetrachloride. The chlorination can also be run in the absence of a solvent if the cyclodithioacetal is a liquid or a solid with an m.p. of less than 100° C.

Conveniently, the cyclodithioacetal and the organic solvent are charged into a suitable reaction vessel equipped with means for stirring and heating. The reaction mixture is then conveniently heated to an elevated temperature, e.g., to reflux, and the chlorinating agent is added slowly with stirring. After the addition of the chlorinating agent is complete, the reaction mixture is conveniently stirred for a short period of time, e.g. 1 to 2 hours at reflux. After completion of the reaction, the mixture is cooled to room temperature. The substituted benzotrichloride product can be isolated using standard laboratory procedures. Conveniently, water is added to the mixture and the organic layer separated by phase separation. The organic layer can then be stripped of solvent and the product purified by suitable standard procedures, such as distillation or fractional crystallization.

Benzotrichloride compounds prepared by the process of the present invention can be intermediates in the manufacture of benzoyl chlorides and benzotrifluorides which are known useful compounds as dyestuff intermediates, herbicide intermediates, and producing hydroxy benzophenone ultraviolet light stabilizers.

The following examples are presented to illustrate the present invention as well as some of the various embodiments of the invention. These examples are presented as being illustrative of the novel process of the invention and are not intended to be a limitation as to the scope thereof.

EXAMPLE 1

Preparation of 2-(3-Methylphenyl)-1,3-Dithiolane

Anhydrous HCl was bubbled rapidly for about 5 minutes through a solution of 46.87 gm (0.39 moles) of 3-methylbenzaldehyde and 44.92 gm (0.477 moles) of 1,2-ethanedithiol in 300 ml of $CHCl_3$. During the addition of HCl, there was a slight exotherm with a rise in temperature to about 60° C. After completion of the addition of HCl, the reaction was stirred for 1 hour at room temperature, washed twice with 100 ml portions of water, dried with $MgSO_4$, and fractionated to give 54.55 gm (0.278 moles) of a clear, colorless liquid (71% yield) b.p. 108°–110° C. (0.2 mm/Hg). Elemental analysis for $C_{10}H_{12}S_2$:

|  | C | H |
|---|---|---|
| Calculated: | 61.16 | 6.16 |
| Found: | 61.22 | 6.20 |

EXAMPLE 2

Preparation of 2-(4-Nitrophenyl)-1,3-Dithiolane

Following the general procedure employed in Example 1, 38.58 gm (0.255 moles) of 4-nitrobenzaldehyde and 24.71 gm (0.262 moles) of 1,2-ethanedithiol gave, after crystallization from absolute EtOH, 49.23 gm (0.2169 moles) of an orange colored solid (85% yield) m.p. 80°–82° C. Elemental analysis for $C_9H_9NO_2S_2$:

|  | C | H | N |
|---|---|---|---|
| Calculated: | 47.54 | 3.99 | 6.16 |
| Found: | 47.63 | 4.01 | 6.15 |

EXAMPLE 3

Preparation of 2-(2-Chlorophenyl)-1,3-Dithiolane

Following the general procedure described in Example 1, 55.3 gm (0.393 moles) of 2-chlorobenzaldehyde and 37.21 gm (0.395 moles) of 1,2-ethanedithiol gave, after distillation, 65.65 gm (0.303 moles) of a clear, colorless liquid, b.p. 121°–125° C. (0.03 mm/Hg). Elemental analysis for $C_9H_9ClS_2$:

|  | C | H |
|---|---|---|
| Calculated: | 49.85 | 4.19 |
| Found: | 50.59 | 4.24 |

EXAMPLE 4

Preparation of 2-(4-Methoxyphenyl)-1,3-Dithiolane

Following the general procedure as in Example 1, 25 gm (0.184 moles) of 4-methoxybenzaldehyde and 17.3 gm (0.184 moles) of 1,2-ethanedithiol gave, after crystallization from hexane, 39.3 gm (0.183 moles) of a white colored solid (96% yield) m.p. 62°–63° C. Elemental analysis for $C_{10}H_{12}OS_2$:

|  | C | H |
|---|---|---|
| Calculated: | 56.56 | 5.70 |
| Found: | 56.82 | 5.59 |

EXAMPLE 5

Preparation of 2-(α-Naphthyl)-1,3-Dithiolane

Following the general procedure as in Example 1, 38.27 gm (0.245 moles) of α-naphthaldehyde and 23.58 gm (0.25 moles) of 1,2-ethanedithiol gave, after evacuating the volatiles, 54.56 gm (0.235 moles) of an orange colored oil (96% yield).

EXAMPLE 6

Preparation of 3-Methylbenzotrichloride 0.38 moles of sulfuryl chloride in an equal volume of carbon tetrachloride was added dropwise to 21.6 gm (0.11 moles) of 2-(3-methylphenyl)-1,3-dithiolane dissolved in 22 mls of carbon tetrachloride while refluxing and stirring. After the addition, the reaction mixture was stirred for 1 hour at reflux and allowed to cool to room temperature. The solvent was evacuated and the residue Kugelrohr distilled at 65°–70° C. (0.43 mm/Hg) to give 18.32 gm (89.9% yield) of product. NMR and Gas Chromatograph/Mass Spectrometry (GC/MS) Analysis: $^1H$—NMR ($CCl_4$) δ2.27 (S, $CH_3$), 6.9 to 7.2 and 7.5 to 7.65 (m$_+$ 4H, aryl protons); GCMS (70 ev), M/e (% rel. int.) 212 (M +4, 4), 210 (M+ +2, 12), 208 (M+, 13), 177 (13), 175 (79), 173 (100), 138 (15), 103 (26), 102 (25), 101 (19), 87 (20), 86 (16), 77 (23), 75 (19), 69 (22), 68 (24), 51 (64).

EXAMPLE 7

Preparation of 4-Nitrobenzotrichloride 6.67 gm (0.029 moles) of the dithiolane of Example 2 was reacted following the procedure of Example 6. Analysis of the crude reaction mixture by $'H$—NMR revealed the presence of 4-nitro-benzotrichloride in ≧95% yield. The product was not isolated. NMR and GC/MS Analysis for Product: $^1H$—NMR ($CDCl_3$), δ7.99 (d, J=9.8 Hz, 2H), 8.2 (d, J=9.8 Hz, 2H); GCMS (70 ev), M/e (% rel. int.) 241 (M+ +2, 2.2), 239 (M+, 2.3), 206 (72), 204 (100), 148 (16), 146 (23), 125 (17), 123 (56), 75 (13), 73 (22).

EXAMPLE 8

Preparation of 2-Chlorobenzotrichloride 11.4 gm (0.053 moles) of the dithiolane of Example 3 was reacted following the procedure of Example 6 to give 6.12 gm of a 3.2:1 mixture of 2-chlorobenzotrichloride and 2-chlorobenzaldichloride (b.p. 85°-98° C. at 0.05 mm/Hg). In repetitive reactions the yield of 2-chlorobenzotrichloride varied from 61% to 30%. NMR and GC/MS Analysis for Product: $^1$H—NMR (CDCl$_3$) δ7.2 to 7.6 (complex multiplet, 3H), 8.1 to 8.25 (complex multiplet, 1H); GCMS (70 ev), M/e (% rel. int.) 232 (M+ +4, 10.4), 230 (M+ +2, 19.6), 228 (M+, 15.2), 197 (67), 195 (100), 193 (91), 125 (16), 123 (50), 99 (14), 97 (48), 96 (22), 73 (26), 62 (28), 61 (38).

EXAMPLE 9

Preparation of 4-Methoxybenzotrichloride 5.8 gm (0.0274 moles) of the dithiolane of Example 4 was reacted following the procedure of Example 6 to give 5.01 gm of a 3.8:1 mixture of 3-methoxybenzaldichloride and 3-methoxybenzotrichloride (b.p. 83°-84° C. at 0.3 mm/Hg). NMR and GC/MS Analysis for Product: $^1$H—NMR (CDCl$_3$), δ3.63 (S, 3H, OCH$_3$), 6.7 (d, J=13.5 Hz, 2H), 7.65 (d, J=13.5 Hz, 2H); GCMS (70 ev), M/e (% rel. int.) 228 (M+ +4, 3.3), 226 (M+ +2, 9.2), 224 (M+, 9), 193 (17), 191 (93), 189 (100).

EXAMPLE 10

Preparation of 1-Trichloromethylnaphthylene 14.66 gm (0.063 moles) of the dithiolane of Example 5 was reacted following the procedure of Example 6 to give 13.26 gm of an oil (b.p. 80°-100° C. at 0.05 mm/Hg) which contained 57.2% 1-dichloromethylnaphthylene and 33.4% 1-trichloromethylnaphthylene. GC/MS Analysis for Product: GCMS (70 ev), M/e (% rel. int.) 248 (M+ +4, 3.2), 246 (M+ +2, 11.7), 244 (M+, 12.2), 211 (67), 209 (100), 139 (35), 106 (11), 104 (17), 69 (32).

Although this invention has been described with respect to specific embodiments, the details thereof are not to be construed as limitations for it will be apparent that various embodiments, changes, and modifications may be resorted to without departing from the spirit and scope thereof, and it is understood that such equivalent embodiments are intended to be included within the scope of this invention.

I claim:
1. A process for the preparation of a substituted benzotrichloride which comprises the steps of:
   (a) reacting a substituted benzaldehyde with a compound having the formula HS—(CH$_2$)$_n$—SH in the presence of an acid;
   (b) reacting the product of step (a) with a chlorinating agent to form a substituted benzotrichloride wherein in the above formula n is an integer from 2 to 3.
2. The process according to claim 1 wherein n is 2.
3. The process according to claim 1 wherein the acid is a mineral acid.
4. The process according to claim 3 wherein the mineral acid is hydrogen chloride.
5. The process according to claim 1 wherein the acid is a Lewis acid.
6. The process according to claim 5 wherein the Lewis acid is boron trifluoride.
7. The process according to claim 1 wherein the substituted benzaldehyde is 3-methylbenzaldehyde.
8. The process according to claim 1 wherein the substituted benzaldehyde is 2-chlorobenzaldehyde.
9. The process according to claim 1 wherein the substituted benzaldehyde is 4-methoxybenzaldehyde.
10. The process according to claim 1 wherein the substituted benzaldehyde is α-naphthaldehyde.
11. The process according to claim 1 wherein the substituted benzaldehyde is 4-nitrobenzaldehyde.
12. The process according to claim 1 wherein the product of step (a) is chlorinated with sulfuryl chloride.
13. A process for the preparation of 3-methylbenzotrichloride which comprises the steps of:
   (a) reacting 3-methylbenzaldehyde with 1,2-ethanedithiol in the presence of an acid;
   (b) reacting the product of step (a) with a chlorinating agent to form 3-methylbenzotrichloride.
14. The process according to claim 13 wherein the acid is hydrogen chloride.

* * * * *